United States Patent [19]
Grisoni

[11] Patent Number: 5,899,513
[45] Date of Patent: May 4, 1999

[54] PRECISION TWEEZERS WITH REMOVABLE TERMINALS

[75] Inventor: Franco Grisoni, Vacallo, Switzerland

[73] Assignee: Ideal-Tek S.A., Chiasso, Switzerland

[21] Appl. No.: 09/067,917

[22] Filed: Apr. 29, 1998

[30] Foreign Application Priority Data

Jul. 17, 1997 [CH] Switzerland .............................. 1750/97

[51] Int. Cl.⁶ ..................................................... B25B 9/02
[52] U.S. Cl. ............................................................ 294/99.2
[58] Field of Search ................................ 294/86.4, 99.2, 294/902; 606/205–207, 210, 211

[56] References Cited

U.S. PATENT DOCUMENTS

| | | | |
|---|---|---|---|
| 420,125 | 1/1890 | Swain | 294/99.2 |
| 2,157,226 | 5/1939 | Betz | 294/99.2 |
| 3,818,784 | 6/1974 | McClure | 294/99.2 |
| 4,634,165 | 1/1987 | Russell et al. | 294/99.2 |
| 5,334,215 | 8/1994 | Chen | 606/210 |
| 5,458,387 | 10/1995 | Conway et al. | 294/902 |

*Primary Examiner*—Dean Kramer
*Attorney, Agent, or Firm*—Young & Thompson

[57] ABSTRACT

The invention relates to a pair of precision tweezers (1) with two tines (2, 3), each of which has a terminal (10, 11), each terminal (10, 11) having a pair of calibrated cylindrical projections (10*i*, 11*i*) capable of entering a pair of holes (4, 5 and 6, 7) in the respective tine (2, 3), wherein the pair of holes (6, 7) in one (3) of tines (2, 3) is comprised of a hole which is cylindrical (6) and a hole which is oblong (7) in the transverse direction with respect to the longitudinal axis of said tine (3), and the pair of holes (4, 5) in other tine (2) is comprised of two holes which are oblong in the direction of the longitudinal axis of the tine.

3 Claims, 2 Drawing Sheets

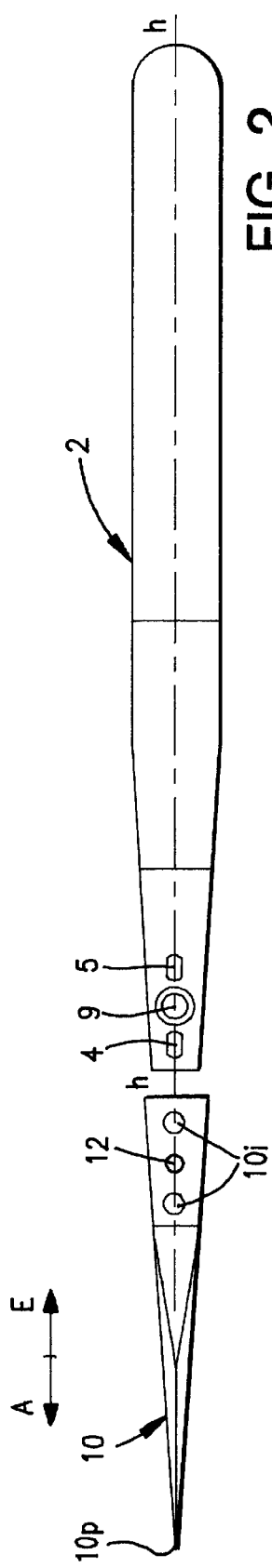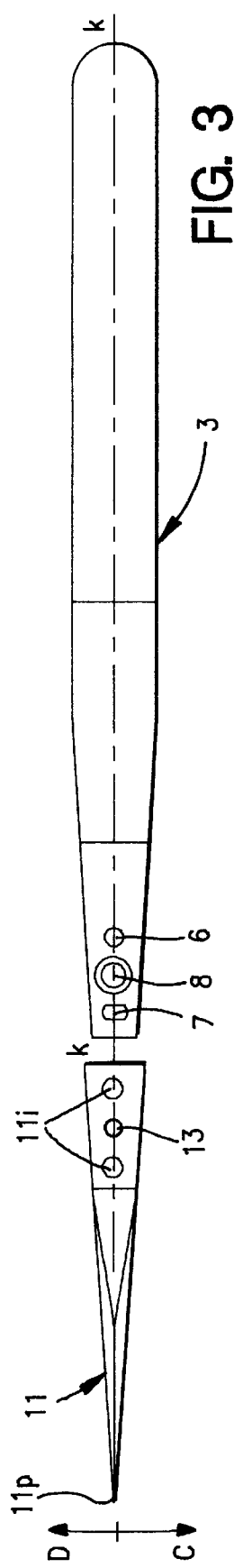

PRECISION TWEEZERS WITH REMOVABLE TERMINALS

This invention relates to the field of precision tweezers with two terminals attached reversibly on the free ends of the two tines which form the tweezers.

To obtain an exact alignment between the terminals themselves and between the terminals and the respective tines, on each of the latter—according to the prior art—there is a pair of calibrated cylindrical holes parallel to one another, into which are inserted cylindrical projections, also calibrated, which are joined to the terminal to which it will be attached.

Once the precise alignment of the parts has been determined, the terminals are then secured to the tines using a known attachment system, for example one comprised of a screw and holes present on the tine and on the terminal, the hole on the latter being threaded.

This attachment system is obtained by leaving predetermined spaces between the screw and the hole in the tine in such a way as to allow attachment of the parts after having defined the alignment, independently of a possible shifting between the axes of the two holes, one of which, as was mentioned above, is threaded, and through which the attachment screw passes.

This system of alignment and attachment yields a sufficient degree of precision when the terminals are made of metal, but has some limitations when for example these terminals, whether made of metal or ceramic materials, are heat-treated to improve physical characteristics, for the purpose of obtaining better resistance to wear, better resistance to combined compressive and bending stress, and better electrical or thermal conductivity, etc.

In this case, between the two terminals of a pair of tweezers such as this one, due to the residual internal (not necessarily isotropic) stresses in the material after said heat treatments, dimensional differences may appear, manifested either in total length or in alignment with the respective tines.

This in turn leads to imperfect superposition of the points of the terminals on the assembled tweezers, with a noticeable adverse effect on the precision of the delicate operations the tweezers are designed to carry out.

To avoid the aforementioned disadvantages, the inventor of this invention has designed a pair of precision tweezers which always enable perfect superposition of the points, whether or not there are dimensional differences between the two terminals.

This is accomplished by making the holes with a particular shape and with particular dimensions which allow the terminals to be aligned so as to ensure the aforementioned desired result. This will be explained in further detail below.

In particular, the object of this invention is a pair of precision tweezers as defined in the preamble of claim 1 appended hereto, characterized by the characterizing part of this claim.

One preferred embodiment of the invention will be described below. It is to be understood that although a preferred embodiment of the invention has been described, various other embodiments and variations may occur to those skilled in the art. Any such other embodiments and variations which fall within the scope and spirit of the present invention are intended to be covered by the claims. In this description reference will be made to the attached diagrams which show the following:

FIG. 2 shows an exploded view of the top of the tweezers from FIG. 1;

FIG. 3 shows an exploded view of the bottom of the tweezers from FIG. 1;

FIG. 4 shows an enlarged front view of the series of three holes present on one of the tines;

FIG. 5 shows an enlarged front view of the series of three holes present on the other tine.

Figure 1:
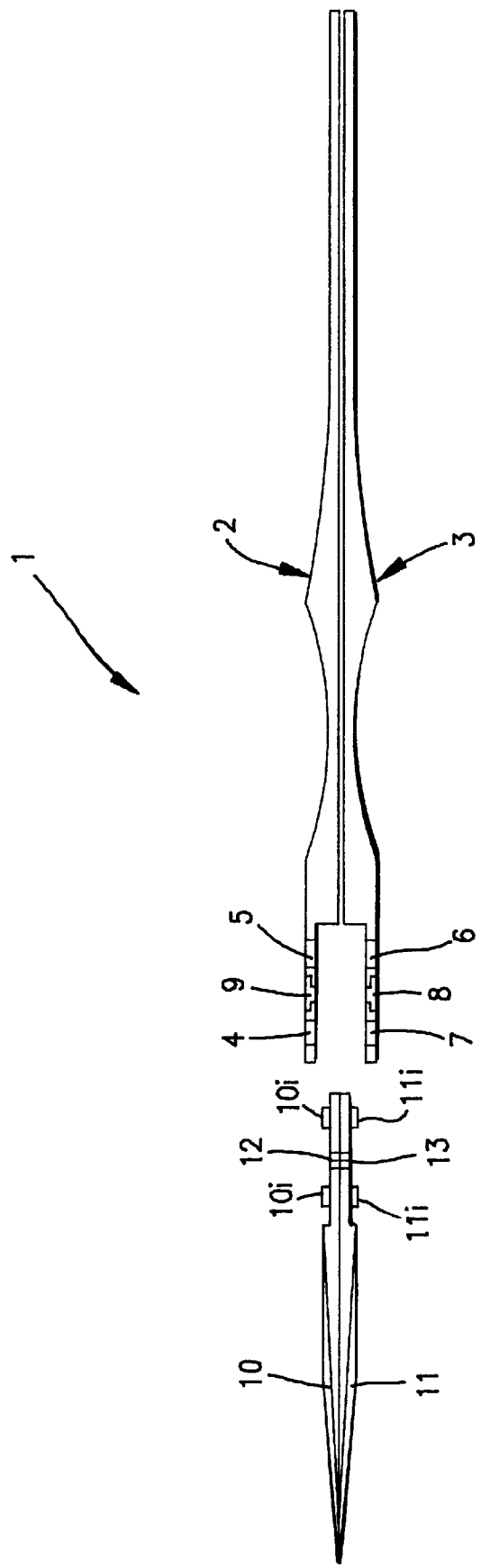
FIG. 1 shows a lateral exploded view of a pair of tweezers according to the invention.

It can be observed in FIG. 2 that at the end of tine 2 there are three holes aligned with one another: center hole 9 is shaped in such a way as to accommodate, with a predetermined amount of play, the head of an attachment screw (not shown).

The two holes 4, 5 arranged laterally on either side of this center hole 9 have a width extending in a direction transverse to longitudinal axis h—h of tine 2 enabling snug accommodation of two cylindrical projections $10i$ present on terminal 10 which are to be attached, but are oblong (therefore in an approximately elliptical shape) in the direction of this axis h—h, in such a way as to allow a predetermined degree of axial travel of the entire projection $10i$ (see arrows A–E) when they are inserted in these holes 4, 5 (an enlarged view of aforementioned holes 4, 5, 9 is given in FIG. 4).

It can be observed in FIG. 3 moreover that at the end of other tine 3 there are three holes in alignment: center hole 8 is identical in function and shape to hole 9 described above, but of holes 6, 7 arranged laterally on either side of the center hole, hole 6 which is farther away from the free end of tine 3 is cylindrical, and calibrated in such a way as to snugly accommodate one of two cylindrical projections $11i$ of terminal 11 which are to be attached to tine 3, and hole 7 closer to the free end of tine 3 has a width extending in the direction of longitudinal axis K—K of the latter slightly greater than or equal to the diameter of other cylindrical projection $11i$ of the terminal, and has a greater length, therefore being oblong in the direction perpendicular to this axis K—K, so as to allow a predetermined degree of travel of the projection coupled to it in two opposite directions (see arrows C–D) transversely to this longitudinal axis K—K of tine 3.

In other words, when projections $11i$ are inserted in holes 6, 7, one of them, the one inserted in cylindrical hole 6, can rotate around its own axis, and the other inserted in oblong hole 7 can travel in one of the aforementioned directions C or D.

Since this travel actually delineates the arc of a circle with very small diameter, hole 7 is consequently made like a rest on the circle arc: given the extremely small dimensions of the travel it is still possible to obtain the desired adjustability with hole 7 of approximately elliptical shape as in FIG. 5 and with a width in the direction of this axis K—K just slightly greater than the diameter of these cylindrical projections $11i$.

These projections can also have various diameters with consequently diverse sizes of the actual holes, still yielding the same results.

With pair of precision tweezers 1 as described above, and as shown in FIG. 1, it is possible to do the following: two terminals 10, 11 are installed on respective tines 2, 3; before tightening the aforementioned attachment screws (not shown) in the respective pairs of aligned holes 9–12 and 8–13 (of which 12, 13 of terminals 10, 11 are threaded), the positioning of terminal 10 is adjusted in directions A–E along the h—h axis of tine 2 in such a way that its point $10p$ is precisely superimposed lengthwise on lip of the other terminal 11, which is engaged as a fixed reference element in the longitudinal direction since it cannot travel axially.

The configuration of holes 4 and 5 on tine 2 allows terminal 10—positioned as described above—to be aligned perfectly with this tine 2, and to be perfectly superimposed lengthwise on the other terminal 11, since terminal 10 can be fixed in this position with its above described attachment screw which is not shown in the diagrams.

At this point, if other terminal 11, as the result of small dimensional variations, does not have point 11p perfectly aligned and point 10p of terminal 10 is already attached, all that is required is to rotate it a small amount in the direction of arrows C and D until points 10p and 11p are perfectly superimposed, and then effect definitive attachment with the aforementioned attachment screw, which is not shown.

This invention will allow perfect control of the configuration of the point of precision tweezers 1, whether or not there are small dimensional differences between the two terminals 10, 11, thereby attaining the object which the inventor set for himself.

It is to be understood that although a preferred embodiment of the invention has been described, various other embodiments and variations may occur to those skilled in the art. Any such other embodiments and variations which fall within the scope and spirit of the present invention are intended to be covered by the following claims.

I claim:

1. Precision tweezers (1) with two tines (2, 3), attached to each of which is a terminal (10, 11), each terminal having a pair of calibrated cylindrical projections (10i, 11i) capable of being inserted into a pair of holes (4, 5 and 6, 7) made in the respective tine (2, 3), characterized in that the pair of holes (6, 7) in one (3) of the tines (2, 3) is comprised of a hole which is cylindrical (6) and a hole which is oblong (7) in the transverse direction with respect to longitudinal axis (K—K) of said tine (3), and the pair of holes made on the other tine (2) is comprised of two holes which are oblong (4, 5) in the direction of longitudinal axis (h—h) of the tine.

2. Precision tweezers as claimed in claim 1, wherein the oblong holes (7, 4, 5) have an essentially elliptical form.

3. Precision tweezers as claimed in claim 1 wherein the terminals (10, 11) are made of a ceramic material.

* * * * *